United States Patent
Fearon

(12) 
(10) Patent No.: US 6,187,004 B1
(45) Date of Patent: Feb. 13, 2001

(54) SUBCUTANEOUS BONE EXPANSION DEVICE

(76) Inventor: Jeffrey A. Fearon, 7777 Forest La., C-700, Dallas, TX (US) 75230

( * ) Notice: Under 35 U.S.C. 154(b), the term of this patent shall be extended for 0 days.

(21) Appl. No.: 08/584,909

(22) Filed: Jan. 11, 1996

Related U.S. Application Data

(63) Continuation of application No. 08/091,995, filed on Jul. 14, 1993, now abandoned.

(51) Int. Cl.[7] .................................................. A61B 17/56
(52) U.S. Cl. ......................... 606/57; 606/53; 606/54-59; 606/60; 606/61; 606/69; 606/70; 606/71; 606/102; 606/105
(58) Field of Search ................................ 606/53, 54–59, 606/60, 61, 69, 70, 71, 102, 105

(56) References Cited

U.S. PATENT DOCUMENTS

| 5,129,903 | * | 7/1992 | Luhr et al. | 606/71 |
| 5,201,737 | * | 4/1993 | Leibinger et al. | 606/69 |

FOREIGN PATENT DOCUMENTS

| 988800 | * | 5/1976 | (CA) | 606/105 |
| 1239266 | * | 7/1960 | (FR) | 606/71 |
| 1637774 | * | 3/1991 | (SU) | 606/63 |

* cited by examiner

Primary Examiner—Michael Buiz
Assistant Examiner—David O. Reip

(57) ABSTRACT

A subcutaneous bone expansion device including a stationary plate and an expansion plate, each affixed to bone portions, and an expansion mechanism to vary relative distance between the stationary plate and the expansion plate. The expansion mechanism may be operated from a location remote from the stationary plate and expansion plate. The device may be located almost entirely subcutaneously, except for portions of the expansion mechanism necessary to effect operation of the device. Those portions of the expansion mechanism necessary to effect operation of the device may exit from within the body under the skin at a location remote from the location of the expanding bone portions. The bone expansion is a gradual process. As the bone portions are separated by small distance, distraction of callus between the bone portions generates new bone to fill the gap between the bone portions. The relative distance between the stationary plate and the expansion plate may, from time to time, be varied by operation of the expansion device to allow bone portions to remain sufficiently separated for continual bone generation (by distraction of callus) to fill the gap between the bone portions until a desired bone lengthening is achieved.

8 Claims, 2 Drawing Sheets

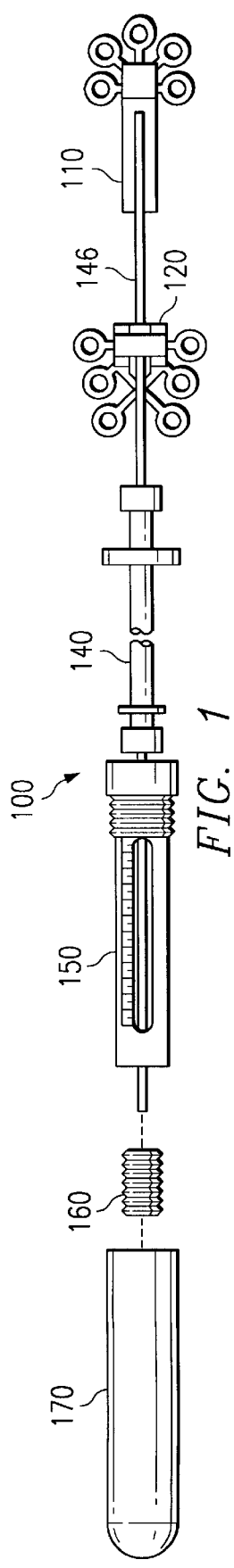
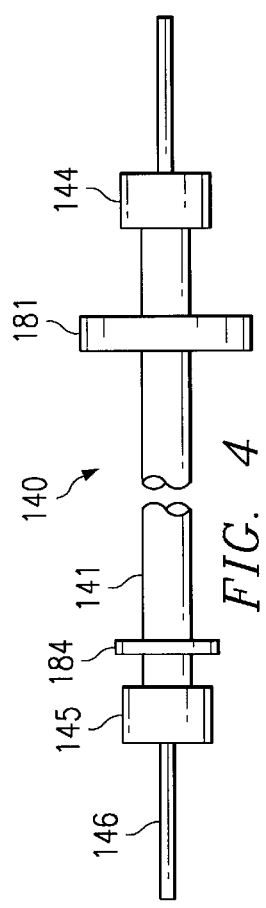
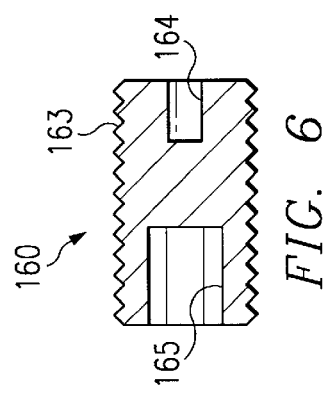
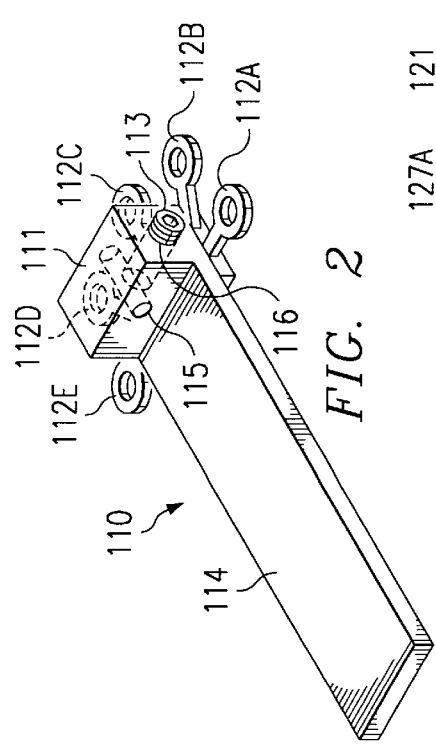
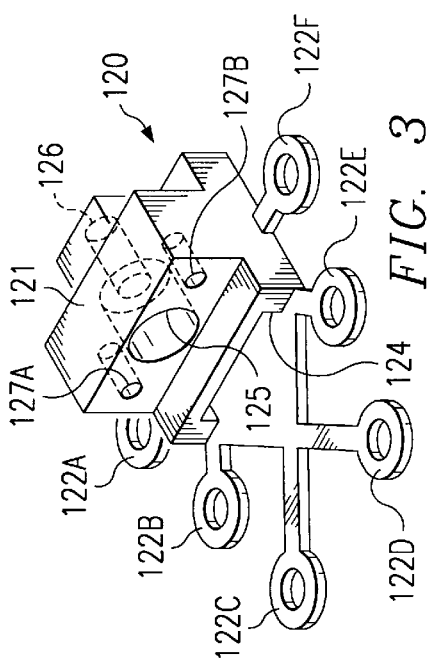

SUBCUTANEOUS BONE EXPANSION DEVICE

This is a continuation of application Ser. No. 08/091,995, filed Jul. 14, 1993, now abandoned.

BACKGROUND OF THE INVENTION

1. Field of the Invention

The invention relates to an orthopedic surgical device and, more particularly, to a device to be used in bone lengthening by bone fracture and gradual distraction of callus.

2. Description of the Related Art

In the 1900s, medical science began experimenting with bone lengthening techniques. Early bone lengthening procedures proved ineffective due to a variety of factors, such as complication by edema, skin necrosis, infection, angular deviation, and delayed ossification of the expanded segment. As a result, medical practitioners abandoned attempts at bone lengthening in favor of practices of cutting complimentary bones to obtain symmetry or using prostheses to compensate for bone length disparity.

Then in the 1950s, Dr. Gavril A. Ilizarov, a Russian physician, developed what is now referred to as the "Ilizarov Technique" for bone lengthening. In the Ilizarov Technique, bones are lengthened by severing the cortex of a bone to be lengthened while minimizing damage to the periosteum and the medullary cavity, and then very gradually separating the separated cortex ends as new bone is generated in the distraction gap. Since the origins of the Ilizarov Technique, considerable advances have been made to techniques and processes of bone lengthening in general keeping with the techniques of Ilizarov.

The original Ilizarov Technique was, in particular, directed primarily to lengthening bones in the leg. In the original Ilizarov Technique, pins were placed through the skin into the bone, bone between the pins was partially cut, and then gradually the pins were pulled apart over a period of many weeks. As a result of this slow expansion, the bone had the opportunity to regenerate, filling in the gradually enlarging gap.

Practice of the Ilizarov Technique is presently limited to only certain cases of bone deformity where lengthening is necessary. Many birth defects involve the skull and facial skeleton. Those birth defects often result from a local growth disturbance in that area. An example of such a birth defect is a forehead which does not grow forward sufficiently to accommodate growth of the child. Those defects can lead to an increase in pressure on the brain as the brain grows and is restricted from further growth by the forehead. Development delays can result from this condition. The typical treatment presently followed in these cases involves a technique, different from the Ilizarov Technique, where bones are cut and moved to another location. This particular technique unfortunately has certain limitations because, with subsequent growth of the patient, in particular where the patient is a growing child, the deformity may recur. In attempts to compensate for the possibility of recurrence of the deformity in these patients, practitioners oftentimes move bones farther than necessary to compensate for expected growth, or other complications result from the technique.

A more recent form of treatment for bone deformities in the skull and facial skeletal region utilizes the Ilizarov Technique. To date, the Ilizarov Technique is known to have been applied to the skull and facial skeletal bones at medical centers in New York and Mexico City. It is believed that the only use to date of the technique in that regard is with children having one side of the jaw which does not grow forward to the extent of the growth of the other jaw side. In the treatment of this particular deformity by means of the Ilizarov Technique, pins are placed through the skin into the jaw, the jawbone is severed, and the severed parts of the jawbone are gradually moved apart, allowing time for the space between the severed parts to fill in with new bone. Employment of the Ilizarov Technique in this manner has certain adverse effects including long stretched out scars that are left in the facial skin from the pins. Additionally, the technique in this instance requires a cumbersome external device, which must be worn by the patient for up to six to eight weeks.

An example of the type device used in current practice of the Ilizarov Technique in these cases is shown in U.S. Pat. No. 5,147,358 to Daniel J. Remmler. This patent, issued in 1992, teaches a skull distraction and fissioning apparatus and method implementing multiple mini-fixation plates attached to a cranial-facial skeleton. As set forth therein, the apparatus and method are for surgically attaching the plates to the skull and then monitoring skull expansion, all as set forth and shown therein. In particular, the Remmler device and method require that plates be surgically attached to the skull through overlying soft skin tissues. As with the other prior art techniques described above for similar treatments or for use with the Ilizarov Technique, use of the device and method of Remmler result in traumatic scarring, like that which resulted from the use of pins in the original Ilizarov Technique.

The present invention exhibits significant improvement in the prior devices and methods for use in practice of the Ilizarov Technique and, in particular, when that technique is used in connection with the skull and facial skeletal bones. The invention provides a device and method of cranial-facial bone expansion utilizing a drive expansion plate system, internally disposed with respect to the skin, having a drive which may be actuated from a single location, which location is remotely disposed from the plate system. Because the plates are mounted internally to the skull with respect to the skin and the actuation mechanism for the drive is remotely disposed from the plates, the invention provides a device and method suitable for practice of the Ilizarov Technique, which device and method substantially reduce, or even eliminate, traumatic scarring and dispose of the necessity that a cumbersome structure be worn by the patient for an extended period.

SUMMARY OF THE INVENTION

In one embodiment, the invention is a device for expanding relative distance between adjacent pieces of bone. The device comprises first means for securement with a first bone piece, second means for securement with a second bone piece, and means for changing relative positioning of the first means with respect to the second means, thereby changing relative positioning of the first bone piece with respect to the second bone piece.

In another aspect, the means for changing is operable from a location remote from the first means and the second means.

In even another aspect, the first means and the second means are secured subcutaneously with the first bone piece and the second bone piece, respectively.

In yet another aspect, the means for changing comprises a tube means fixed in relationship to the first means and moveable relative to the second means and a wire means fixed in relationship to the second means and moveable relative to the first means.

In even another aspect, the changing relative positioning of the first bone piece to the second bone piece is along a linear course.

In a further aspect, the first means and the second means are secured to the bone pieces via screws.

In another further aspect, the means for changing is operable from a location remote from the first means and the second means.

In yet a further aspect, the device further comprises a means for measuring the relative distance between the bone pieces.

In another aspect, the first means includes a tongue and the second means includes an aperture for accepting the tongue, the tongue being slidingly moveable within the aperture to effect movement along the linear course.

In yet another aspect, the device further comprises a means for measuring the relative distance between the bone pieces.

In another aspect, the first means is an expansion plate having a tongue; the second means is a stationary plate having an aperture for accepting the tongue for sliding engagement therewith to effect a linear course of relative movement of the first means and the second means; and the means for changing is a tube having a first end and a second end, the first end being securable with the stationary plate, an adjustment housing, the second end being securable with the adjustment housing, a wire securable with the expansion plate, slidably engaged with the stationary plate, and protruding through the tube and the adjustment housing; and an adjustment screw which may be turned into the adjustment housing thereby causing the wire to move through the adjustment housing, the tube, and the second means to change relative positioning of the first means with respect to the second means.

In yet a further aspect, the device comprises a protective cap for covering the adjustment housing to prevent entry into the device of extraneous substances and materials.

In another embodiment, the invention is a method for expanding relative distance between adjacent pieces of bone. The method comprises the steps of securing a first means with a first bone piece, securing a second means with a second bone piece, and changing relative positioning of the first means with respect to the second means, thereby changing relative positioning of the first bone piece with respect to the second bone piece.

In another aspect, the step of changing is by operations remote from the first means and the second means.

In yet another aspect, the method further comprises the steps of making an incision in skin to allow access to the bone pieces, locating the first means and the second means some distance from the incision, and running a means for changing subcutaneously from the first means to the second means and through the incision to outside the skin.

In a further aspect, the step of changing is by turning an adjustment screw of the means for changing, located outside the skin.

In even a further aspect, the method further comprises the step of measuring the relative distance between the adjacent bone pieces by noting the extent of the turning of the adjustment screw.

The invention also includes the product bone expansion of the methods.

BRIEF DESCRIPTION OF THE DRAWINGS

For a more complete understanding of the present invention and the objects and advantages thereof, reference may now be had to the following description taken in conjunction with the accompanying drawings in which:

FIG. 1 is an exploded view of a subcutaneous bone expansion device in accordance with the principles of the present invention;

FIG. 2 is a perspective view of an expansion plate of the expansion device illustrated in FIG. 1;

FIG. 3 is a perspective view of a stationary plate of the expansion device illustrated in FIG. 1;

FIG. 4 is a plan view of a cable assembly of the expansion device illustrated in FIG. 1;

FIG. 6 is a sectional view of an adjustment screw of the expansion device illustrated in FIG. 1;

DETAILED DESCRIPTION OF DRAWINGS

Figure 5:
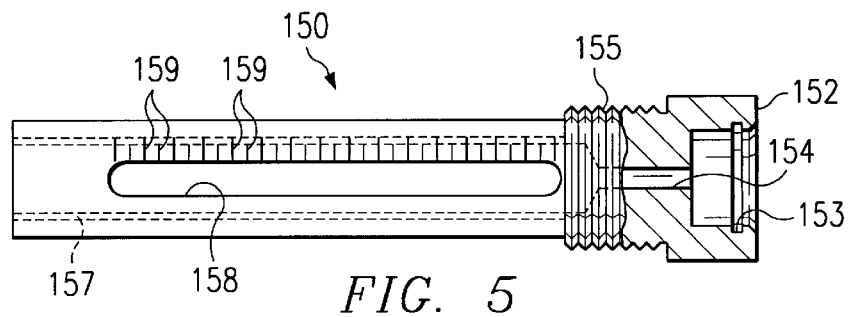
FIG. 5 is a sectional view of an adjustment housing of the expansion device illustrated in FIG. 1.

The following detailed description primarily addresses a preferred embodiment of the subcutaneous bone expansion device of the present invention. Those skilled in the art will, nevertheless, readily recognize that alternative aspects and embodiments of the invention are possible. All those other applications for and embodiments of the invention are hereby expressly included in, and form a part of, the invention.

Referring first to FIG. 1, there is shown an exploded view of a preferred embodiment of the subcutaneous bone expansion device ("expansion device") 100 of the present invention. This preferred expansion device 100 generally comprises an expansion plate 110, a stationary plate 120, a cable assembly 140, an adjustment housing 150, an adjustment screw 160, and a protective cap 170.

Referring now to FIG. 2, there is shown a perspective view of the preferred embodiment of the expansion plate 110 of the invention. The expansion plate 110 has a main body 111 with eyelets 112A–E extending therefrom creating a mounting surface on the underneath side of the eyelets 112A–E. A tongue 114 also extends from the main body 111. Within the main body 111 is a wire aperture 115 for accepting a wire 146 (shown in FIG. 1) and a threaded set screw aperture 116 for accepting a set screw 113. The set screw 113 serves to retain the wire 146 within the wire aperture 115. Clearly, the expansion plate 110 is subject to wide variation in size, design, and application. For example, the expansion plate 110 could include different numbers and arrangement of eyelets 112A–E, as well as different configuration of the main body 111. All these variations, as well as numerous others, are possible and will achieve substantially the same functional objectives and so are included in the invention.

Referring now to FIG. 3, there is shown a perspective view of the preferred embodiment of the stationary plate 120 of the invention. The stationary plate 120 has a main body 121 with eyelets 122A–F extending therefrom, creating a mounting surface on the underneath side. A tongue aperture 124 is formed through the main body 121 and is contoured for a close fit with the tongue 114 of the expansion plate 110 (shown in FIG. 2). A tube aperture 125 is formed partially through the main body 121 on an axis parallel to the tongue aperture 124. A wire aperture 126 is formed through the main body 121, connecting with the tube aperture 125, concentric with the tube aperture 125. The main body 121 also has threaded cable retainer screw apertures 127A–B which are positioned on an axis parallel to the tube aperture 125 and which are located on opposing sides of the tube aperture 125. As with the expansion plate 110 of FIG. 2, the stationary plate 120 is subject to wide variations in design, size, and configuration. Because all these alternatives will achieve substantially the same functional objectives, the alternatives are included in the invention.

Referring now to FIG. 4, there is shown the preferred embodiment of the cable assembly 140 of the invention. The cable assembly 140 generally comprises a tube 141, a tube first end 144, and a tube second end 145. The tube 141 external diameter is smaller than the external diameter of the tube first end 144 and the tube second end 145. Each of the tube 141, the tube first end 144, and the tube second end 145, is hollowed to allow free passage of the wire 146 therethrough. The wire 146 extends beyond the tube ends 144, 145 when inserted in the assembly 140.

Referring now to FIG. 5, there is shown a sectional view of the preferred embodiment of the adjustment housing 150 of the invention. The adjustment housing 150 is generally cylindrical and hollow in shape. One end of the adjustment housing forms a tube receptacle 152. The tube receptacle 152 serves to accept the tube second end 145 of the cable assembly 150 (shown in FIG. 4). The tube receptacle 152 also includes a retainer ring groove 153 and a wire hole 154 concentric with the tube receptacle 152 and extending through into the adjustment end 156. The tube receptacle is also formed with external threads 155. The other end of the adjustment housing 150 is formed with threading along the internal diameter thereof. A slot 158 in the adjustment housing 150 exposes the internal threading to external view. The adjustment housing 150 is equipped with gauge markings 159 positioned externally on the adjustment housing 150 next to the slot 158.

Referring now to FIG. 6, there is shown a sectional view of the preferred embodiment of the adjustment screw 160 of the invention. The adjustment screw 160 is cylindrical in shape and has external threads 163. One end of the adjustment screw 160 is formed with a recess 164 for accepting an end of the wire 14 (shown in FIG. 4). The other end of the adjustment screw is formed with a hex aperture 165. The external threads 163 are adapted for engaging the threading along the internal diameter of the adjustment housing 150 (shown in FIG. 5).

Figure 7:
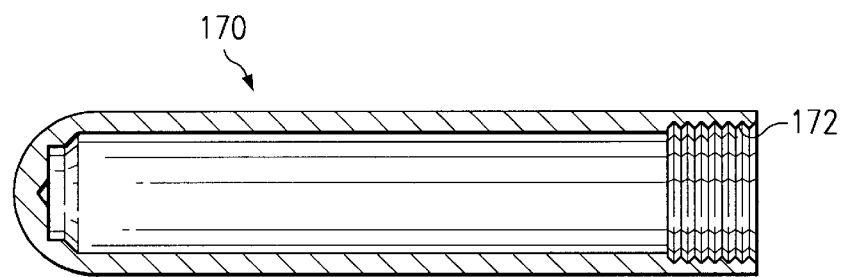
FIG. 7 is a sectional view of the protective cap of the expansion device illustrated in FIG. 1.

Referring now to FIG. 7, there is shown a sectional view of the preferred embodiment of the protective cap 170 of the present invention. The protective cap 170 is generally hollow and cylindrical in shape. One end of the protective cap 170 is fitted with threading 172 along the internal diameter. The other end of the protective cap 170 is closed. The threading 172 of the protective cap 170 serves to engage the external threads 155 of the adjustment housing 150 (shown in FIG. 5).

Referring now to FIGS. 1–7 in combination, the components of the expansion device 100 are preferably formed from stainless steel. However, other materials which will provide the necessary strength and compatibility with the internal environment of the human body may alternatively or additionally be used. Examples of alternate materials could include titanium, plastic, or other inert materials, as well as others.

Referring now to FIGS. 1–3 in combination, the preferred interfacing of the expansion plate 110 with the stationary plate 120 can be better understood. The tongue 114 of the expansion plate 110 engages the tongue aperture 124 of the stationary plate 120. This interfacing of the tongue 114 with the tongue aperture 124 allows the expansion plate 110 to only move linearly towards and away from the stationary plate 120. Although this preferred embodiment of the present invention employs this tongue 114 and aperture 124 arrangement to govern relative movement of the expansion plate 110 and stationary plate 120, other means which allow a linear, or other select, relative movement of the expansion plate 110 with respect to the stationary plate 120, could be employed.

Referring now to FIGS. 1–4 in combination, it can be seen how, in the preferred embodiment, the cable assembly 140 interfaces with the expansion plate 110 and the stationary plate 120. The tube first end 144 inserts into the tube aperture 125 of the stationary plate 120. The wire 146 then extends through the wire aperture 126 of the stationary plate 120. The cable assembly 140 is held stationary with respect to the stationary plate 120 by a retainer washer 181 (see FIG. 4). The retainer washer 181 has an internal diameter smaller than the diameter of the tube first end 144 but at least as large as the diameter of the tube 141. The retainer washer 181 may be retained in place against the main body 121 of the stationary plate 120 by screws (not shown) engaging the threaded cable retainer screw apertures 127A–B. In this manner, the tube first end 144 is held in place within the tube aperture 125 of the stationary plate 120 by the retainer washer 181 and the tube 141 will remain stationary with respect to the stationary plate 120. It should be noted that other means of securing the tube first end 144 to the stationary plate 120 can be used both in terms of the particular securing apparatus and design and configuration of the pieces.

Referring still to FIGS. 1–4 in combination, in the preferred embodiment, the wire 146 is inserted into the wire aperture 115 of the expansion plate 110. A set screw 113 is threaded into the threaded set screw aperture 116 until it engages the wire 146. In this manner, the wire 146 is held stationary with respect to the expansion plate 110. It can be seen that because the tube 141 is stationary with respect to the stationary plate 120, and the wire 146 is stationary with respect to the expansion plate 110, by moving the wire 146 with respect to the tube second end 145 of the cable assembly 140, the wire 146 will move relative to the tube first end 144 causing the expansion plate 110 to move linearly with respect to the stationary plate 120. Although a set screw 113 has been used in the preferred embodiment to fix the wire 146 stationary relative to the expansion plate 110, any alternative means that can accomplish this objective could be used and all such alternative means are included in the invention.

Referring now to FIGS. 1, 4, and 5 in combination, it can be seen how, in the preferred embodiment, the cable assembly 140 interfaces with the adjustment housing 150. The adjustment housing 150 includes a hollow chamber 157. The tube second end 145 inserts into the tube receptacle 152, and the wire 146 inserts through the wire aperture 154. A retainer ring 184 (shown in FIG. 4) engages the retainer ring groove 153 of the tube receptacle 152, thereby holding the tube 141 stationary with respect to the adjustment housing 150. Although a retainer ring is used for securing the tube 141 with respect to the adjustment housing 150, any other means that accomplishes similar objectives could also be used and all such means are included in the invention.

Referring now to FIGS. 1, 4, 5, and 6 in combination, it can be seen how, in the preferred embodiment, the adjustment screw 160 interfaces with the adjustment housing 150 and the cable assembly 140. The wire 146 extends through the adjustment housing 150. The recess 164 of the adjustment screw 160 accepts wire 146 extending from the adjustment housing 150. The external threads 163 of the adjustment screw 160 engage the threading along the internal diameter of the adjustment housing 150. The adjustment screw 160 is threaded into the adjustment housing 150 until visible through the slot 158 of the adjustment housing 150, with the wire 146 extending into the recess 164 of the adjustment screw 160. The adjustment screw 160 can be threaded into or out of the adjustment housing 150 using the hex aperture 165 of the adjustment screw 160 by a hex wrench of suitable size for fitting in and turning the adjustment screw. By selecting an appropriate thread pitch for the threading along the internal diameter of the adjustment housing 150 and the adjustment screw external threads 163, each revolution of the adjustment screw 160 will represent a select linear progress of the wire 146 through the adjustment housing 150. The gauge markings 159 of the adjustment housing 150 are spaced and selected so as to represent the select progress of the wire 146 through the adjustment housing 150. Because the wire 146 remains fixed in relation to the expansion plate 110 but may move in relation to the stationary plate 120 and the adjustment housing 150 and cable assembly 140 remains fixed in relation to the stationary plate 120 but may move in relation to the expansion plate 110, the gauge markings 159 allow accurate measurement of the position of adjustment screw 160 and therefore of the relative positioning of the stationary plate 120 and the expansion plate 110. As previously described, the tongue 114 (shown in FIG. 2) and tongue aperture 124 (shown in FIG. 3) restrict relative movement of the stationary plate 120 and expansion plate 110 to essentially only a linear movement. Alternative means of measuring and controlling relative movement are possible and all those means are included herein.

Referring now to FIGS. 1, 5, and 7 in combination, it can be seen how, in the preferred embodiment, the protective cap 170 interfaces with the adjustment housing 150. The open end of the protective cap 170 slides over the end of the adjustment housing 150 until the threading 172 of the protective cap 170 engages the external threads 155 of the adjustment housing 150. When the threading 172 engages the external threads 155, the adjustment housing 150 resides within the opening of the protective cap 170, thereby enclosing and protecting the adjustment housing 150 from entry of extraneous substances.

Figure 8:
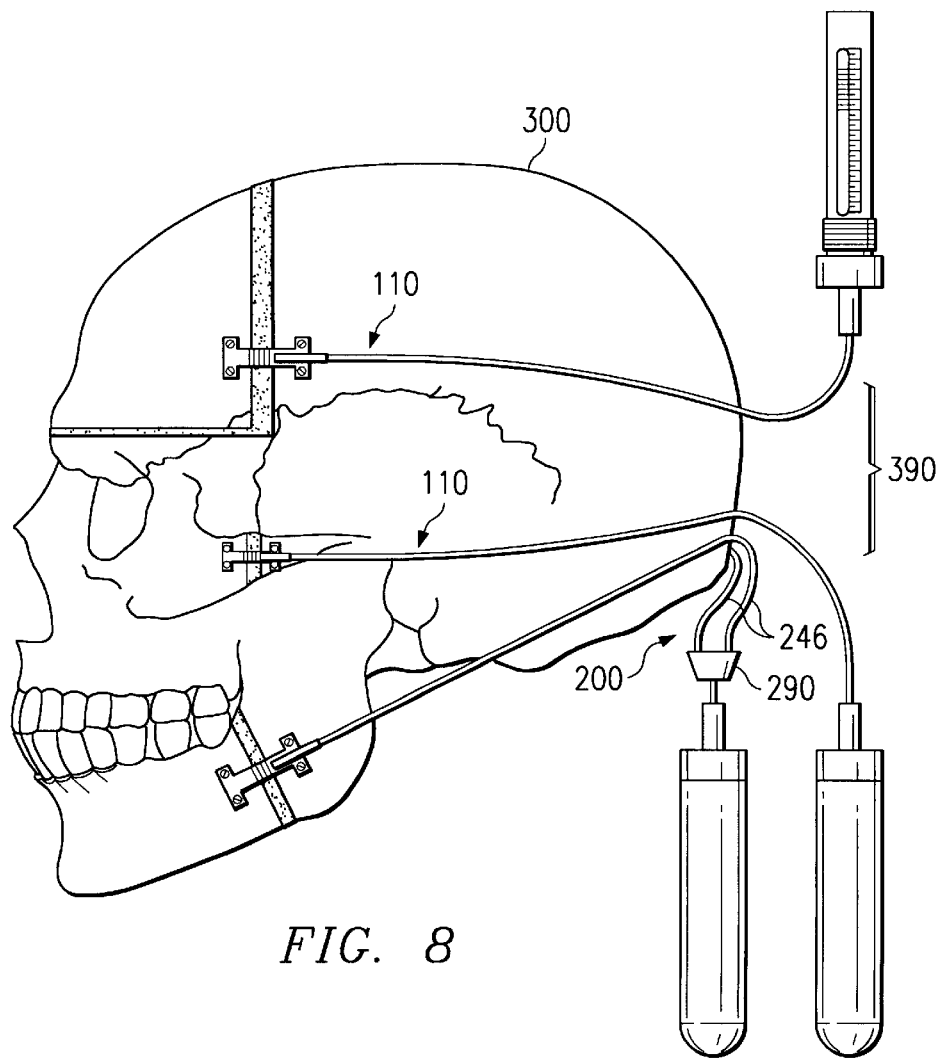
FIG. 8 is a plan view of a skull, illustrating the use of the expansion device of FIG. 1 and the use of an alternative embodiment of the present invention.

Referring now to FIGS. 1, 3 and 8 in combination, it can be seen how the expansion device 100 may interface with a skull 300. It should be understood that these device-skull interface illustrations are intended solely as examples; the expansion device 100 can alternately be positioned on other portions of the skull, or even other bones of the body, as desired to accomplish select bone movement for bone expansion procedures. In the example illustrated, the expansion device 100 is mounted to the skull 300 via the stationary plate 110 and expansion plate 120 by screws or other attachment means. The expansion device 100 is entered under the patient's skin through a remote area of the head, such as the rear scalp area 390. Although the expansion device 100 could be mounted through most any areas of the body, by mounting through a remote area, such as the rear scalp area 390 in the case of skull mountings, any surgical scars will be located only in hidden or less apparent locations of a subject patient. In the preferred embodiment, the stationary plate 110 and expansion plate 120 are entered through a surgical incision and the skin is pulled back to locate proper placement at bone. The stationary plate 110 and expansion plate 120 are then affixed to select locations of bone and connected with the tube 140 via the retainer washer 121. The skin is then allowed to return to its normal position so that the expansion device 100 remains under the patient's skin. Because the expansion device 100 only passes under the skin through the remote area of the incision, obvious and apparent scarring during the bone lengthening process is eliminated or substantially reduced. In employing the bone expansion method using the expansion device 100, the skull 300 must have a gap 310 separating bone portions of the skull 300. The expansion plate 110 and the stationary plate 120 are located on the skull 300 on opposing sides of the gap between the portions. Mounting screws (not shown) pass through the expansion plate eyelets 112A–E and the stationary plate eyelets 122A–F and into the skull 300, thereby securing the expansion device 100 to the skull 300. Although mounting screws are used in this particular embodiment, other means including, without limitation, adhesives, pins, and others, which can sufficiently secure the expansion plate 110 and the stationary plate 120 to the skull 300 or other applicable bone, may additionally or alternatively be employed without departing from the purposes and scope of the invention. All those other means are included in the invention. After securing the expansion plate 110 and the stationary plate 120 to the skull 300, the cable assembly 140 is routed out of the remote area, for example, the rear scalp area 390 in the example of FIG. 8, thereby disposing the adjustment housing 150 outside of the patient's body. Because the cable assembly 140 and the adjustment housing 150 are disposed outside of the patient's body at a remote location during use, the invention is less cumbersome to the patient during the bone regeneration process than were the prior art devices.

Referring still to FIGS. 1–3 and 8 in combination, as the gap between bone portions of the skull 300 (or other bone) is filled with repair bone (i.e., distraction of callus) generated by the body, the relative distance between the stationary plate 120 and expansion plate 110 of the expansion device 100 is expanded by turning the adjustment screw 160 into the adjustment housing 150. The adjustment screw 160 is threaded into the adjustment housing 150 using a tool in the adjustment screw's hex aperture 165 until the gap is expanded to the desired width as represented by the gauge markings 159 on the adjustment housing 150.

Because the adjustment housing is disposed outside of the patient's body, expansion of the gap can usually be performed from time to time without subjecting the patient to further surgery. The expansion of the gap is periodically repeated as the body increases the extent of bone regeneration, until the final desired size of bone growth within the gap is achieved. Once the final desired bone growth is achieved within the gap, the expansion device 100 is removed through a remote area of the head, such as the rear scalp area 390 of the skull 300, thereby reducing the visible scarring from use of the device 100.

As can be seen in FIG. 8, the expansion device 100 could be used in a wide variety of areas of the skull 300. As an example, the expansion device 100 can also be used on a facial plate or for extending the length of a jaw. In addition, use of the device 100 is not limited to the facial bones or skull, as the device 100 is similarly useful in lengthening any bone, wherever located.

Referring still to FIG. 8, there can be seen an alternate embodiment of the present invention. Expansion areas on the skull 300, such as the jaw (or other bones of the skull or body), often require expansion of corresponding areas on the opposite side of the skull 300 (or body). Therefore, it is often desirous to have an expansion device 200 that will simultaneously extend on dual sides of the skull (or body). In this alternate embodiment, the expansion device 200 is equipped with dual expansion plates and dual stationary plates, which plates are controlled by a cable assembly having dual wires 246. The cable assembly includes a divider 290 for translating the motion or movement of an adjustment screw in the adjustment housing to the plates. It can be seen that use of the expansion device 200 will provide simultaneous and identical extension of multiple areas of the skull 300 (or other bones), as opposed to the expansion device 100 which serves only to extend single areas. The procedures applicable with the expansion device 100 are similarly applicable to use of the expansion device 200.

As is clearly seen, the present invention provides a device and method suitable for practice of the Ilizarov Technique, which device and method substantially reduce, or even eliminate, traumatic scarring and dispose of the necessity that a cumbersome structure be worn by the patient for an extended period. The present invention is believed to be especially effective when configured and employed as described herein, however, those skilled in the art will readily recognize that numerous variations and substitutions may be made in the invention and its use and configuration to achieve substantially the same results as achieved by the embodiments and, in particular, the preferred embodiments, expressly described herein. Each of those variations is intended to be included in the description herein and forms a part of the present invention. The foregoing detailed description is, thus, to be clearly understood as being given by way of illustration and example only, the spirit and scope of the present invention being limited solely by the appended claims.

What is claimed is:

1. A device comprising:

an expansion plate having a tongue;

a stationary plate having an aperture for accepting said tongue for sliding engagement therewith to effect a linear course of relative movement of said expansion plate and said stationary plate; and a tube having a first end and a second end, said first end being securable with said stationary plate, an adjustment housing, said second end being securable with said adjustment housing, a wire securable with said expansion plate, slidably engaged with said stationary plate, and protruding through said tube and said adjustment housing;

and an adjustment screw which may be turned into said adjustment housing thereby causing said wire to move through said adjustment housing, said tube, and said stationary plate to change relative positioning of said expansion plate with respect to said stationary plate; and wherein said expansion plate is adapted for attachment with a first bone piece and said stationary plate is adapted for attachment with a second bone piece;

wherein said tube is adapted for containment within a skin in a vicinity of said skin underlaid by said expansion plate, said first bone piece, said stationary plate, and said second bone piece, and is adapted for passage through said skin remotely from said vicinity of said skin; and wherein said device is adapted to virtually eliminate scarring of said skin in said vicinity of said skin.

2. The device of claim 1, further comprising a protective cap for covering said adjustment housing to prevent entry into said device of extraneous substances and materials.

3. The device of claim 1, wherein said tube includes screw threads secured with said tube and a screw secured with said wire, wherein turning said screw in said screw thread causes said wire to move longitudinally within said tube, causing said first plate and said second plate to change in linear relative positioning.

4. The device of claim 1, wherein change in linear relative positioning of said expansion plate and said stationary plate is adapted to concomitantly change relative positioning of said first bone piece and said second bone piece.

5. The device of claim 1, wherein said tube is adapted to pass through said skin remotely from said vicinity of said expansion plate and said stationary plate.

6. A method for expanding relative distance between a first bone piece adjacent to a second bone piece contained within a skin and accessed through a first incision, comprising the steps of:

securing a first plate with said first bone piece;

securing a second plate with said second bone piece;

making a second incision in said skin to allow access by a tube to said first bone piece and said second bone piece;

locating said first plate and said second plate some distance from said incision;

running said tube subcutaneously from said first plate to said second plate and through said second incision to outside said skin;

changing relative positioning of said first plate with respect to said second plate, thereby chanting relative positioning of said first bone piece with respect to said second bone piece;

wherein said step of changing includes increasing distance between said first plate and said second plate and said step of changing is accomplished by activity from outside said skin and remotely from said skin underlaid by said first plate and said second plate;

wherein said step of changing is by turning an adjustment screw of said tube, located outside said skin.

7. The method of claim 6 wherein said step of changing is by operations remote from said first plate and said second plate.

8. The method of claim 6, further comprising the step of measuring said relative distance between said first bone piece and said second bone piece by noting the extent of said turning of said adjustment screw.

* * * * *